(12) United States Patent
Rollins et al.

(10) Patent No.: US 9,883,901 B2
(45) Date of Patent: *Feb. 6, 2018

(54) CHARACTERIZING ABLATION LESIONS USING OPTICAL COHERENCE TOMOGRAPHY (OCT)

(71) Applicant: CASE WESTERN RESERVE UNIVERSITY, Cleveland, OH (US)

(72) Inventors: Andrew M. Rollins, Cleveland Heights, OH (US); Christine P. Fleming, Bronx, NY (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/674,539

(22) Filed: Mar. 31, 2015

(65) Prior Publication Data

US 2015/0202002 A1    Jul. 23, 2015

Related U.S. Application Data

(63) Continuation of application No. 12/844,944, filed on Jul. 28, 2010, now Pat. No. 9,089,331.

(Continued)

(51) Int. Cl.
| | |
|---|---|
| *A61B 18/18* | (2006.01) |
| *A61B 18/12* | (2006.01) |
| *A61B 5/00* | (2006.01) |
| *A61B 18/14* | (2006.01) |
| *A61B 17/00* | (2006.01) |
| *A61B 18/00* | (2006.01) |
| *A61B 18/02* | (2006.01) |
| *A61B 18/20* | (2006.01) |
| *A61B 90/00* | (2016.01) |

(52) U.S. Cl.
CPC ............ *A61B 18/12* (2013.01); *A61B 5/0066* (2013.01); *A61B 5/6852* (2013.01); *A61B 18/1492* (2013.01); *A61B 18/02* (2013.01); *A61B 18/20* (2013.01); *A61B 2017/00243* (2013.01); *A61B 2018/00351* (2013.01); *A61B 2018/00702* (2013.01); *A61B 2090/3735* (2016.02)

(58) Field of Classification Search
CPC ......... A61B 18/18; A61B 18/20; A61B 18/24; A61B 18/245; A61B 18/14; A61B 2018/00315; A61B 2018/00351; A61B 2018/00571; A61B 2018/00577
USPC ........... 606/4–18, 21–23, 41–45; 607/88–92, 607/96–112; 128/898
See application file for complete search history.

(56) References Cited

U.S. PATENT DOCUMENTS

| | | | |
|---|---|---|---|
| 6,241,722 B1 * | 6/2001 | Dobak | A61B 18/02 606/20 |
| 9,089,331 B2 * | 7/2015 | Rollins | A61B 5/0066 |

(Continued)

*Primary Examiner* — Ahmed Farah
(74) *Attorney, Agent, or Firm* — Tarolli, Sundheim, Covell & Tummino LLP

(57) ABSTRACT

Systems, methods, and other embodiments associated with characterizing Radio Frequency Ablation (RFA) lesions using Optical Coherence Tomography (OCT) are described. One example method includes acquiring an OCT signal from a Region Of Interest (ROI) in an ablated material. The example method may also include determining whether a lesion was formed by the ablation by analyzing optical properties of the ROI as recorded in the OCT signal.

16 Claims, 15 Drawing Sheets

Related U.S. Application Data

(60) Provisional application No. 61/230,281, filed on Jul. 31, 2009.

(56) References Cited

U.S. PATENT DOCUMENTS

| | | | | |
|---|---|---|---|---|
| 2001/0027316 | A1* | 10/2001 | Gregory | A61B 18/24 606/15 |
| 2004/0054358 | A1* | 3/2004 | Cox | A61F 9/00806 606/5 |
| 2004/0092830 | A1* | 5/2004 | Scott | A61B 5/0066 600/478 |
| 2006/0058622 | A1* | 3/2006 | Tearney | A61B 5/0062 600/407 |
| 2008/0024788 | A1* | 1/2008 | Shimizu | A61B 5/0066 356/497 |
| 2008/0095714 | A1* | 4/2008 | Castella | A61B 5/0066 424/9.3 |
| 2009/0214615 | A1* | 8/2009 | Zhao | A61L 31/10 424/423 |
| 2010/0158339 | A1* | 6/2010 | Omori | A61B 1/00009 382/131 |
| 2011/0144524 | A1* | 6/2011 | Fish | A61B 18/1492 600/547 |
| 2011/0267583 | A1* | 11/2011 | Hayashi | G01B 9/02028 351/206 |
| 2013/0072928 | A1* | 3/2013 | Schaer | A61B 8/4281 606/41 |

* cited by examiner

CHARACTERIZING ABLATION LESIONS USING OPTICAL COHERENCE TOMOGRAPHY (OCT)

CROSS REFERENCE TO RELATED APPLICATIONS

This application is a Continuation of U.S. patent application Ser. No. 12/844,944, entitled "CHARACTERIZING ABLATION LESIONS USING OPTICAL COHERENCE TOMOGRAPHY (OCT)", filed Jul. 28, 2010, which claims the benefit of U.S. Provisional Application 61/230,281, filed Jul. 31, 2009. The entire contents of each of these disclosures are hereby incorporated by reference.

GOVERNMENT FUNDING

This invention was made with government support under Grant Nos. HL008304 and HL085939 awarded by The National Institutes of Health. The United States government has certain rights in the invention.

BACKGROUND 2.5 million people in the U.S. have cardiac arrhythmias that cannot be controlled with traditional treatments. Ablation is one treatment for cardiac arrhythmias. Ablation destroys tissue that triggers or supports abnormal electrical pathways in tissue. Cardiac ablation attempts to target and eradicate the tissue of the abnormal electrical pathway, while avoiding normal tissue. Conventional ablation techniques use low-resolution images acquired by fluoroscopy or static images from computed tomography merged onto fluoroscopy. These techniques monitor the ablation by measuring tissue temperature, impedance at the surface of the tissue, and other indirect methods. Indirect methods of monitoring the ablation may result in delivering more lesions than necessary and prolonging procedure times. Traditionally, directly visualizing critical intra-cardiac structures in the heart when performing ablation was not feasible.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Systems, apparatus, and methods associated with determining whether a lesion is present in a material are described.

References to "one embodiment", "an embodiment", "one example", "an example", indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic. The physical manipulations create a concrete, tangible, useful, real-world result.

It has proven convenient at times, principally for reasons of common usage, to refer to these signals as bits, values, elements, symbols, characters, terms, and numbers. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
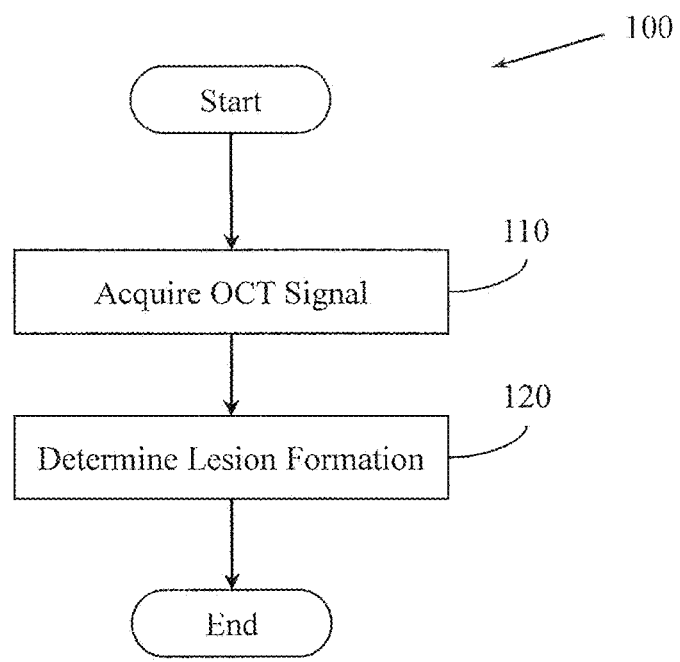
FIG. 1 illustrates an example method associated with determining whether a lesion is present in a material.

FIG. 1 illustrates a method 100 associated with determining whether a lesion is present in a material. Method 100 may include, at 110, acquiring an Optical Coherence Tomography (OCT) signal from a Region of Interest (ROI) in a material subjected to ablation. The ablation may be, for example, Radio Frequency Ablation (RFA), High Intensity Focused Ultrasound (HIFU) ablation, laser ablation, or cryoablation. The material may be tissue, for example, myocardial tissue, skeletal muscle tissue, intestinal tissue, and so on. In tissue, ablation may cause necrosis of the tissue at the ablation point. This necrosis may create a lesion that has different optical properties than normal non-ablated tissue.

For example, myocardium is covered by a thin layer, called the epicardium, which appears highly reflective within OCT images. Normal myocardium has a characteristic birefringence artifact, due to the highly organized structure of fibers in the myocardium. Epicardial fat has a heterogeneous appearance within OCT images. Adipose tissue is covered by a layer of epicardial cells and connective tissue that appears as a bright layer within OCT images. Coronary vessels appear as signal poor regions, corresponding to the empty vessel lumens embedded in a layer superficial to the myocardium. The location of the vessel lumens correspond with the location of the vessels apparent in microscope images.

The distinct features of the epicardium, myocardium, epicardial fat and coronaries are visible within slices parallel to the epicardial surface, and correlate to the microscope images of the surface. Within the images, a thick epicardial layer is observed which covers epicardial fat, which in turn surrounds the coronary vessel. Untreated myocardium is characterized by a polarization artifact and an epicardial layer and a coronary vessel images encompassing epicardial fat, which appears heterogeneous. Therefore, viable tissue is characterized by a polarization artifact dark band within conventional OCT images due to the birefringence property of the highly organized myocardial tissue.

However, ablated myocardial tissue has different optical properties. Specifically, with the application of RF energy and lesion formation, the contrast between the epicardium and myocardium and the polarization dependent artifact is lost. Moreover, an ablated region of myocardial tissue impedes the conducting of an electrical signal through part of the tissue. Ablating a region of myocardial tissue that abnormally conducts an electrical signal is therefore useful in treating arrhythmias. Thus, method 100 may be used to treat myocardial arrhythmias in an intra-cardiac RFA procedure.

Method 100 may also include, at 120, controlling an apparatus to determine whether a lesion was formed by the ablation. Determining whether a lesion was formed is performed by analyzing optical properties of the ROI as recorded in the OCT signal. The difference in optical properties between viable non-ablated tissue and ablated tissue is useful in determining whether ablation of a region of tissue was successful in forming a lesion. The optical properties of the ROI that may be analyzed may include, for example, birefringence, anisotropy, absorption, light attenuation rate, backscattering, tissue scattering, mean intensity, and tissue heterogeneity.

The optical properties of the ROI as recorded in the OCT signal also facilitate determining tissue architecture. Tissue architecture may include, for example, fiber orientation, epicardial fat and structures including coronary vessels, atrio-ventricular nodes, and sino-atrial nodes.

Determining whether the lesion was formed includes applying signal-processing techniques to the OCT signal. For example, the OCT signal may be processed by applying a single scattering model, or a Laplacian of Gaussian (LoG) to the OCT signal. Applying signal-processing techniques to the OCT signal provides values for the optical properties. These values facilitate determining whether a lesion exists in the material from the ablation. Determining whether a lesion exists may also include determining a lesion size, and a lesion depth from the optical properties.

Indications of a lesion may include, for example, a decrease in birefringence, an increased signal intensity, a decreased signal attenuation rate, a decreased gradient strength, an increased heterogeneity, an increased scattering, and an increased imaging depth. Birefringence may be detected by filtering with a LoG to quantify gradient strength with a conventional OCT system; signal differences in the two channels of a polarization diverse detection OCT system; and retardance measurements using a polarization sensitive OCT system. An attenuation coefficient may facilitate calculating a lesion depth. The attenuation coefficient may indicate tissue scattering. In one example, the attenuation coefficient increases with an increasing lesion depth. A backscattering coefficient may indicate reflectivity. A correlation coefficient can quantify how well an OCT signal fits a mathematical model of light-tissue interaction. The correlation coefficient may indicate heterogeneity.

A Region of Interest (ROI) may be, for example, a portion of material that is being ablated, a portion of material that was ablated, or a portion of material that may be ablated. Acquiring an OCT signal from a ROI prior to ablating the ROI facilitates controlling an apparatus to determine whether to target the ROI for ablation, or to avoid ablating the ROI. Ablation of a ROI that includes, for example, coronary vessels may be avoided by acquiring and processing an OCT signal from the ROI prior to ablation.

Acquiring the OCT signal may include using Polarization Sensitive OCT (PS-OCT), a polarization diverse detection OCT system, a conventional OCT, or Fourier Domain OCT (FDOCT). Example FDOCT systems include spectral domain FDOCT systems (SDOCT) and swept source FDOCT systems (SSOCT). The optical properties of the ROI recorded in the OCT signal may also include retardation, and a spectral interference pattern.

While FIG. 1 illustrates various actions occurring in serial, it is to be appreciated that various actions illustrated in FIG. 1 could occur substantially in parallel. By way of illustration, a first process could acquire the OCT signal, and a second process could determine whether a lesion is present. While two processes are described, it is to be appreciated that a greater and/or lesser number of processes could be employed and that lightweight processes, regular processes, threads, and other approaches could be employed.

In one example, a method may be implemented as computer executable instructions. Thus, in one example, a computer-readable medium may store computer executable instructions that if executed by a machine (e.g., processor) cause the machine to perform a method that includes determining whether a lesion was generated by an ablation in the ROI as a function of optical properties of the ROI as registered in the OCT signal. While executable instructions associated with the above method are described as being stored on a computer-readable medium, it is to be appreciated that executable instructions associated with other example methods described herein may also be stored on a computer-readable medium.

A "computer readable medium", as used herein, refers to a medium that stores signals, instructions and/or data. A computer readable medium may take forms, including, but not limited to, non-volatile media, and volatile media. Non-volatile media may include, for example, optical disks, and magnetic disks. Volatile media may include, for example, semiconductor memories, and dynamic memory. Common forms of a computer readable medium may include, but are not limited to, a floppy disk, a flexible disk, a hard disk, a magnetic tape, other magnetic medium, an application specific integrated circuit (ASIC), a compact disk CD, other optical medium, a random access memory (RAM), a read only memory (ROM), a memory chip or card, a memory stick, and other media from which a computer, a processor or other electronic device can read.

Figure 2:
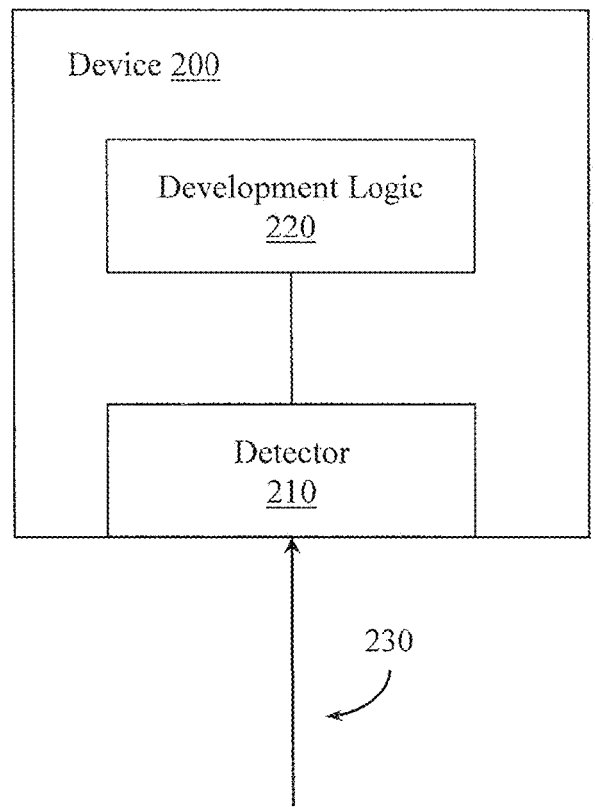
FIG. 2 illustrates an example device associated with determining whether a lesion is present in a material.

FIG. 2 illustrates an example device 200 associated with controlling an apparatus to determine whether a lesion was generated by an ablation in a ROI. Device 200 may include a detector 210 to acquire an OCT signal 230 from a ROI in a material. Device 200 may also include a development logic 220 configured to control an apparatus to determine whether a lesion was generated by an ablation in the ROI based, at least in part, on optical properties of the ROI as registered in the OCT signal 230. The ablation may be, for example, RFA, HIFU ablation, laser ablation, cryoablation, and so on. The material may be myocardial tissue, a tissue that exhibits anisotropic optical properties, and so on.

The development logic 220 determines whether the lesion was generated by applying signal-processing techniques to the OCT signal 230. Processing the OCT signal 230 may result, for example, in determining discrete values for the optical properties of the OCT signal. The optical properties of the ROI that may be provided from this processing are, for example, birefringence, anisotropy, absorption, light attenuation rate, backscattering, tissue scattering, mean intensity, and tissue heterogeneity. These discrete values facilitate determining whether a lesion exists in the material from the ablation. The processing techniques that may be used include a single scattering model, or a Laplacian of Gaussian (LoG). The development logic 220 may also determine a lesion size, and a lesion depth from the OCT signal 230.

The detector 210 acquires the OCT signal 230. In one embodiment the device 200 may be, for example, a conventional OCT, an OCT with polarization diversity detection, a PS-OCT, or a FDOCT. The OCT may use a superluminescent diode (SLD) centered at 1310 nm with a 70 nm (FWHM) bandwidth as a light source.

Alternatively, the OCT may use a system having a light source centered at 1310 nm with 70 nm bandwidth and a microscope integrated spectral domain OCT. Spectral interferograms may be acquired with a linearin-wave number ($k=2\pi/\lambda$) spectrometer onto a 1024 pixel line scan camera spectrometer, acquired at a 40 kHz line scan rate. An example system may have a 4.3 mm imaging range, 2 mm-6 dB fall off range, and 110 dB sensitivity. The axial and lateral resolution of the system is 16 and 12 micrometers (in air) respectively. Images may be 4 mm in transverse length, 1000 lines per image, and 512 pixels per line. A volume may consist of 400 images. An index of refraction of 1.38 for ventricular tissue, with the dimensions of the volume being 4 mm×4 mm×3.11 mm (L, W, H), has a corresponding pixel resolution of 4 µm, 10 µm, and 6 µm respectively. Summed voxel projection may be used for rapid visualization of the three dimensional image sets and planes parallel to the sample surface are obtained by detecting the surface with an intensity threshold and digitally flattening the tissue surface.

Detector 210 may also be a detector associated with a conventional OCT, a PS-OCT, or a FDOCT as understood by one of ordinary skill in the art. A low coherence interferometer or a polarimeter may also be used to acquire and analyze signals from a ROI.

Figure 3:
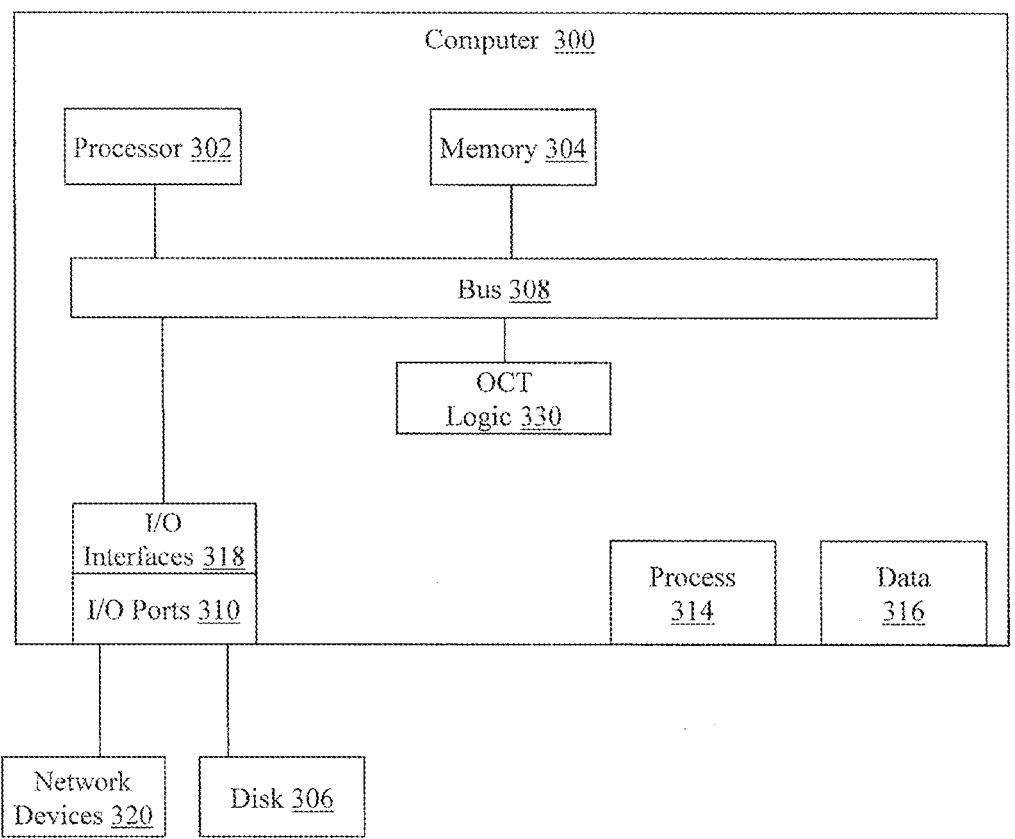
FIG. 3 illustrates an example computing environment in which example systems, apparatus, methods, and equivalents, may operate.

FIG. 3 illustrates an example computing device in which example systems and methods described herein, and equivalents, may operate. The example computing device may be a computer 300 that includes a processor 302, a memory 304, and input/output ports 310 operably connected by a bus 308. In one example, the computer 300 may include an OCT logic 330 configured to control an apparatus to determine whether a lesion was generated by an ablation in the ROI based, at least in part, on optical properties of the ROI as registered in the OCT signal. In different examples, the logic 330 may be implemented in hardware, firmware, and/or combinations thereof. While the logic 330 is illustrated as a hardware component attached to the bus 308, it is to be appreciated that in one example, the logic 330 could be implemented in the processor 302.

Logic 330 may provide means (e.g., hardware, firmware) for acquiring an OCT signal from a ROI in a material. The means may be implemented, for example, as an ASIC programmed to acquire an OCT signal. The means may also be implemented as computer executable instructions that are presented to computer 300 as data 316 that are temporarily stored in memory 304 and then executed by processor 302. Logic 330 may also provide means (e.g., hardware, firmware) for controlling an apparatus to determine whether a lesion exists in the ROI from an ablation as a function of optical properties of the ROI as recorded in the OCT signal.

Generally describing an example configuration of the computer 300, the processor 302 may be a variety of various processors including dual microprocessor and other multiprocessor architectures. A memory 304 may include volatile memory and/or non-volatile memory. Non-volatile memory may include, for example, Read Only Memory (ROM), and Programmable ROM (PROM). Volatile memory may include, for example, Random-Access Memory (RAM), Static RAM (SRAM), and Dynamic RAM (DRAM).

A disk 306 may be operably connected to the computer 300 via, for example, an input/output interface (e.g., card, device) 318 and an input/output port 310. The disk 306 may be, for example, a magnetic disk drive, a solid-state disk drive, a floppy disk drive, a tape drive, a Zip drive, a flash memory card, and a memory stick. Furthermore, the disk 306 may be a Compact Disc ROM (CD-ROM) drive, a CD Recordable (CD-R) drive, a CD ReWritable (CD-RW) drive, and a Digital Versatile Disc ROM (DVD ROM). The memory 304 can store a process 314 and/or a data 316, for example. The disk 306 and/or the memory 304 can store an operating system that controls and allocates resources of the computer 300.

The bus 308 may be a single internal bus interconnect architecture and/or other bus or mesh architectures. While a single bus is illustrated, it is to be appreciated that the computer 300 may communicate with various devices, logics, and peripherals using other busses (e.g., Peripheral Component Interconnect Express (PCIE), 1394, Universal Serial Bus (USB), Ethernet). The bus 308 can be types including, for example, a memory bus, a memory controller, a peripheral bus, an external bus, a crossbar switch, and/or a local bus.

The computer 300 may interact with input/output devices via the i/o interfaces 318 and the input/output ports 310. Input/output devices may be, for example, a keyboard, a microphone, a pointing and selection device, cameras, video cards, displays, the disk 306, and the network devices 320. The input/output ports 310 may include, for example, serial ports, parallel ports, and USB ports.

The computer 300 can operate in a network environment and thus may be connected to the network devices 320 via the i/o interfaces 318, and/or the i/o ports 310. Through the network devices 320, the computer 300 may interact with a network. Through the network, the computer 300 may be logically connected to remote computers. Networks with which the computer 300 may interact include, but are not limited to, a Local Area Network (LAN), a Wide Area Network (WAN), and other networks.

Figure 4:
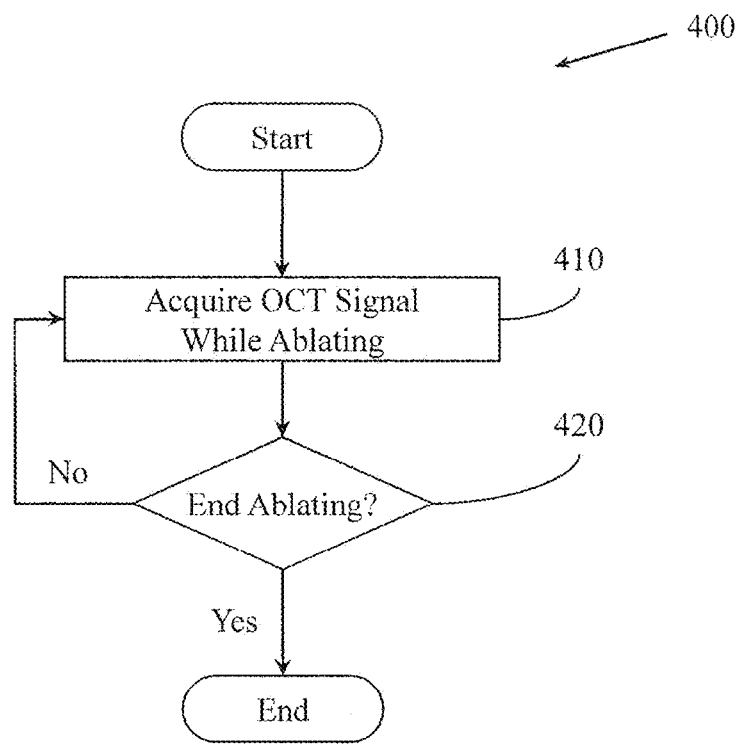
FIG. 4 illustrates an example method associated with real-time OCT imaging of a material.

FIG. 4 illustrates an example method 400 associated with real-time OCT imaging of a material. At 410, method 400 acquires an OCT signal from a ROI in a material while ablating the ROI. The material may be tissue, including myocardial tissue. At 420, method 400 controls an apparatus to stop ablating the ROI. Determining whether to stop the ablating may be based on receiving an input signal, determining whether a lesion has formed from the ablating, or when an onset of complications is detected. Determining whether a lesion has formed is a function of analyzing optical properties of the ROI as recorded in the OCT signal. The optical properties of the ROI may be, for example, birefringence, anisotropy, absorption, light attenuation rate, backscattering, tissue scattering, mean intensity, and tissue heterogeneity. In one embodiment, method 400 may continuously acquire and process OCT signals from the ROI during ablation. In another embodiment, method 400 may intermittently acquire and process OCT signals from the ROI during ablation. This real-time acquiring and processing of OCT signals facilitates forming lesions in the treatment of arrhythmia in myocardial tissue by ablation.

Figure 5:
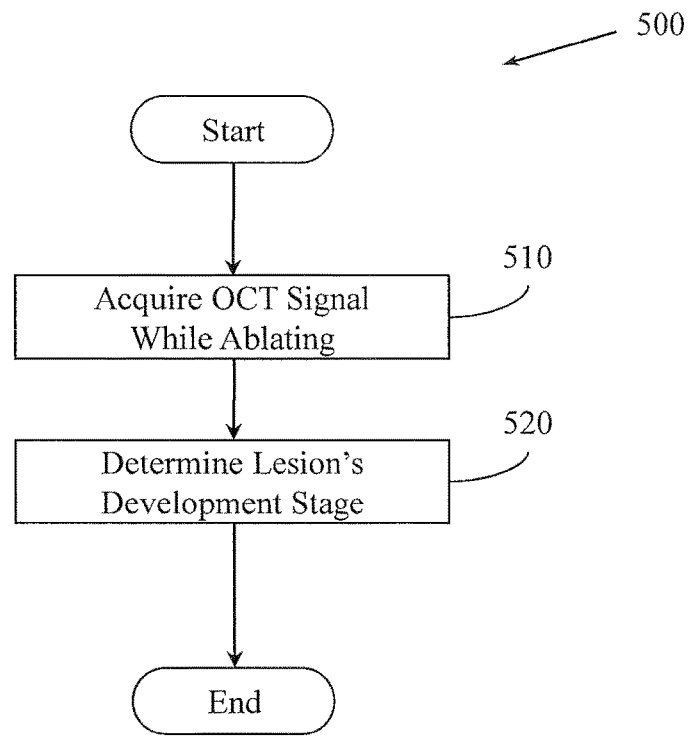
FIG. 5 illustrates an example method associated with using real-time OCT to determine a lesion's development stage.

FIG. 5 illustrates an example method 500 associated with determining a lesion's development stage using real-time OCT. At 510, method 500 acquires an OCT signal from a ROI in a material while ablating the ROI. Method 500 controls an apparatus, at 520, to determine a lesion's development stage in the ROI as a function of optical properties of the ROI as recorded in the OCT signal. Ablating the ROI to form a lesion may be viewed as a gradual process. The lesion progresses through different development stages while ablating the ROI. For example, the lesion begins as a small disturbance while initially ablating the ROI. Continuing to ablate the ROI causes the lesion to progress. After a variable amount of time, the lesion will reach a desirable characteristic. The lesion may progress to an undesirable development stage if ablating is allowed to continue beyond an appropriate time. Lesion development progression in an ROI can be correlated with changes in optical properties and electrical properties of the ROI.

Figure 6:
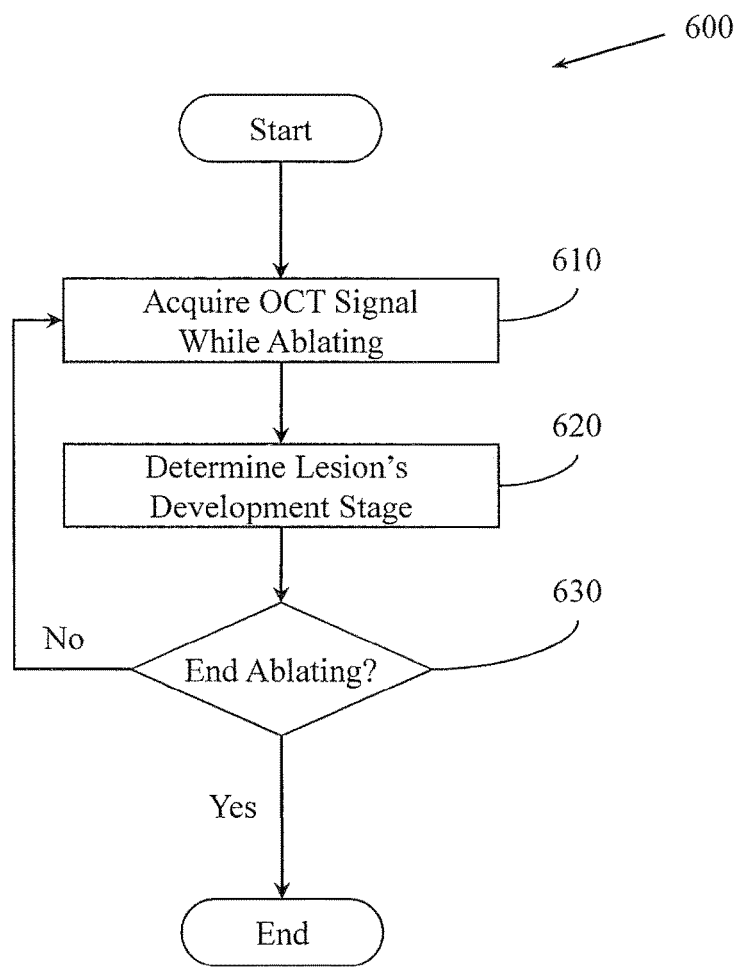
FIG. 6 illustrates another example method associated with using real-time OCT to determine a lesion's development stage and determining when to end ablation based on the real-time OCT image.

FIG. 6 illustrates another example method 600 associated with stopping the ablation of a ROI based on a lesion's development stage. Similar to method 500, method 600 acquires an OCT signal from an ROI in a material during ablation, at 610. At 620, method 600 controls an apparatus to determine a lesion's development stage in the ROI. The lesion's development stage may be determined based on, for example, optical properties of the ROI as recorded in the OCT signal. The optical properties of the ROI are, for example, birefringence, anisotropy, absorption, light attenuation rate, backscattering, tissue scattering, and tissue heterogeneity.

Determining the lesion's development stage from optical properties of the ROI may include calculating, for example, a decrease in birefringence, an increased signal intensity, a decreased signal attenuation rate, a decreased gradient strength, an increased heterogeneity, an increased scattering, and an increased imaging depth. An attenuation coefficient may facilitate calculating a lesion depth. The attenuation coefficient may indicate tissue scattering. In one example, the attenuation coefficient increases with an increasing lesion depth. A backscattering coefficient may indicate reflectivity. A correlation coefficient can quantify how well an OCT signal fits a mathematical model of light-tissue interaction. The correlation coefficient may indicate heterogeneity. The amount of change in the optical properties indicates the lesion's development stage. The optical properties gradually change as the lesion progresses during ablation. For example, birefringence may be detected by filtering with a LoG to quantify gradient strength with a conventional OCT system; signal differences in the two channels of a polarization diverse detection OCT system; and retardance measurements using a polarization sensitive OCT system. A gradual decrease of birefringence as ablation continues indicates a lesion progressing through development stages. Determining a lesion's development stage may also include determining a lesion size, and a lesion depth.

At 630, method 600 controls the apparatus to stop ablating the ROI when it is determined that the lesion is a clinically relevant lesion, or a borderline overtreatment lesion. Overtreatment may be characterized, for example, by disruptions in the myocardium and increased tissue heterogeneity. A clinically relevant lesion is, for example, a lesion that changes the electrical properties of the ROI to impede conducting an electrical signal across the ROI. Ideally, a clinically relevant lesion does not exhibit signs of overtreatment. Overtreatment of an ROI may include, for example, steam pops, or craters in the ROI. Determining the lesion is a borderline overtreatment lesion may include determining an attenuation coefficient and a correlation coefficient for the OCT signal.

Implementing the methods, systems, and devices discussed above may reduce procedure times for treating cardiac arrhythmias, in some cases over eighty percent. In one example, the procedure time using these methods, systems, and devices is less than three hours.

Figure 7:
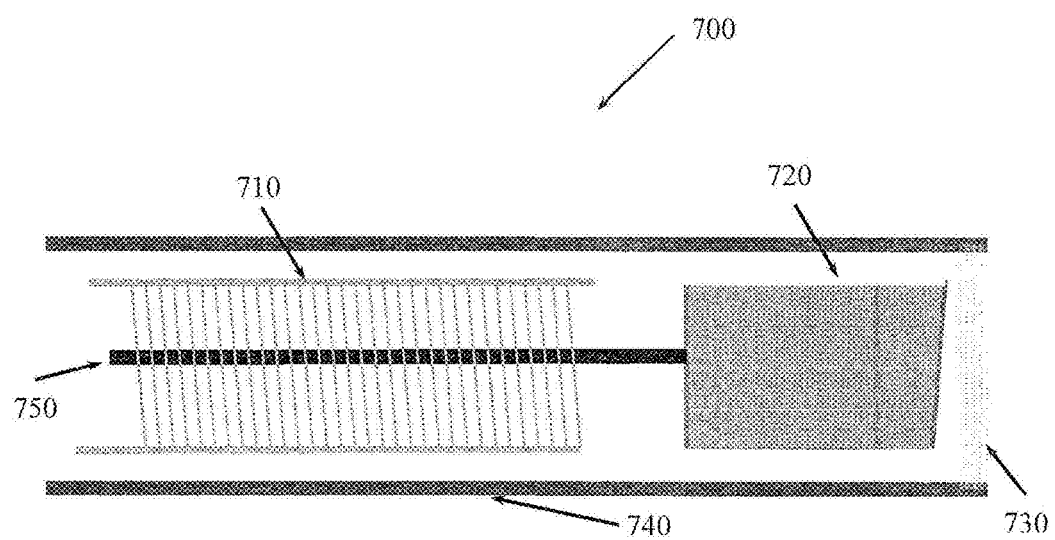
FIG. 7 illustrates an example OCT device for use in a catheter associated with ablating a material and acquiring real-time OCT signals of the material being ablated.

FIG. 7 illustrates an example OCT device optical assembly 700 for use in a catheter associated with ablating a material and acquiring real-time OCT signals of the ablating. The assembly 700 may include, for example, a torsion cable 710. The torsion cable 710 facilitates rotating a Gradient-Index (GRIN) lens 720. In one embodiment, the GRIN lens 720 may be configured to couple to an optical fiber 750. The optical fiber 750 facilitates acquiring OCT signals from a material. The optical window 730 provides protection for the components of OCT device 700 from foreign matter. A sheath 740 provides structure and, similar to the optical window 730, also provides protection from foreign matter. In some embodiments, the assembly 700 is made from Magnetic Resonance Imaging (MRI) and RF energy compatible materials.

Figure 8:
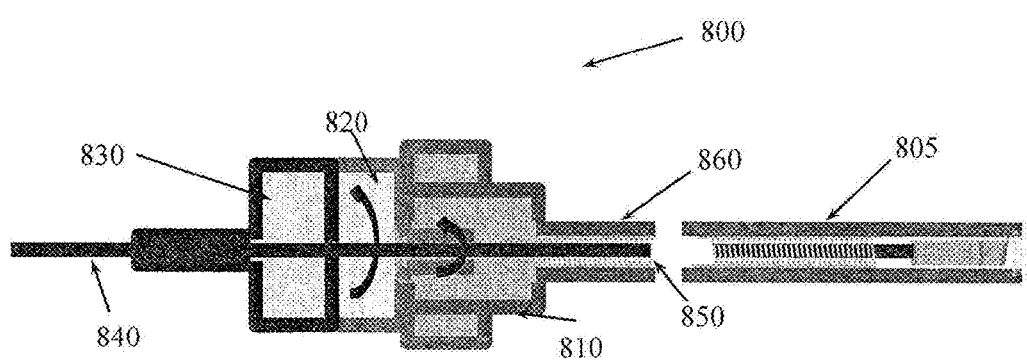
FIG. 8 illustrates an example rotary joint mechanism for rotating an OCT device lens.

FIG. 8 illustrates an example rotary joint mechanism 800 for rotating an OCT device optical assembly 805. The rotary joint mechanism 800 may include, for example, rotary joint 820 for allowing the OCT device optical assembly 805 to rotate. The rotary joint 820 is configured to cause a torsion cable 850 or an optical fiber 840 to rotate and apply torque to the OCT device optical assembly 805 causing the OCT device optical assembly 805 to rotate. The rotary joint mechanism 800 may also include a static sheath holder 810. The static sheath holder 810 prevents a sheath 860 in the OCT device from rotating. The rotary mechanism 800 may also include a static fiber holder 830 to prevent an optical fiber 840 from rotating.

Figure 9:
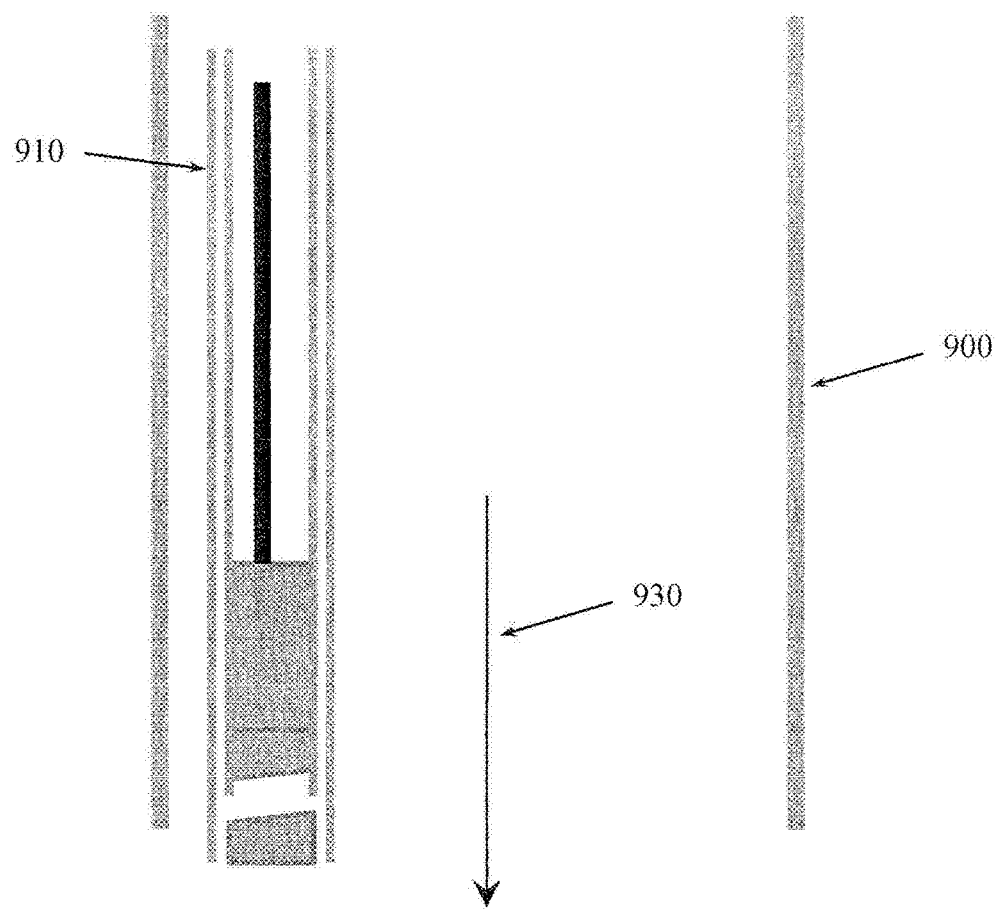
FIG. 9 illustrates an example catheter for acquiring real-time OCT signals and ablating a Region of Interest.

FIG. 9 illustrates an example catheter for acquiring real-time OCT signals and ablating a Region of Interest. The catheter 900 may include an OCT device optical assembly 910 similar to the OCT device optical assembly 700. The catheter 900 is configured to deliver Radio Frequency (RF) energy 930 suitable to ablate a Region of Interest (ROI) from a Radio Frequency Ablation (RFA) device. The catheter 900 is made from Magnetic Resonance Imaging (MRI) and RF energy compatible materials. The catheter 900 facilitates OCT imaging while ablating a ROI with RF energy 930. In some embodiments, the catheter 900 may be miniaturized and integrated into RF or other ablation catheters.

Figure 10:
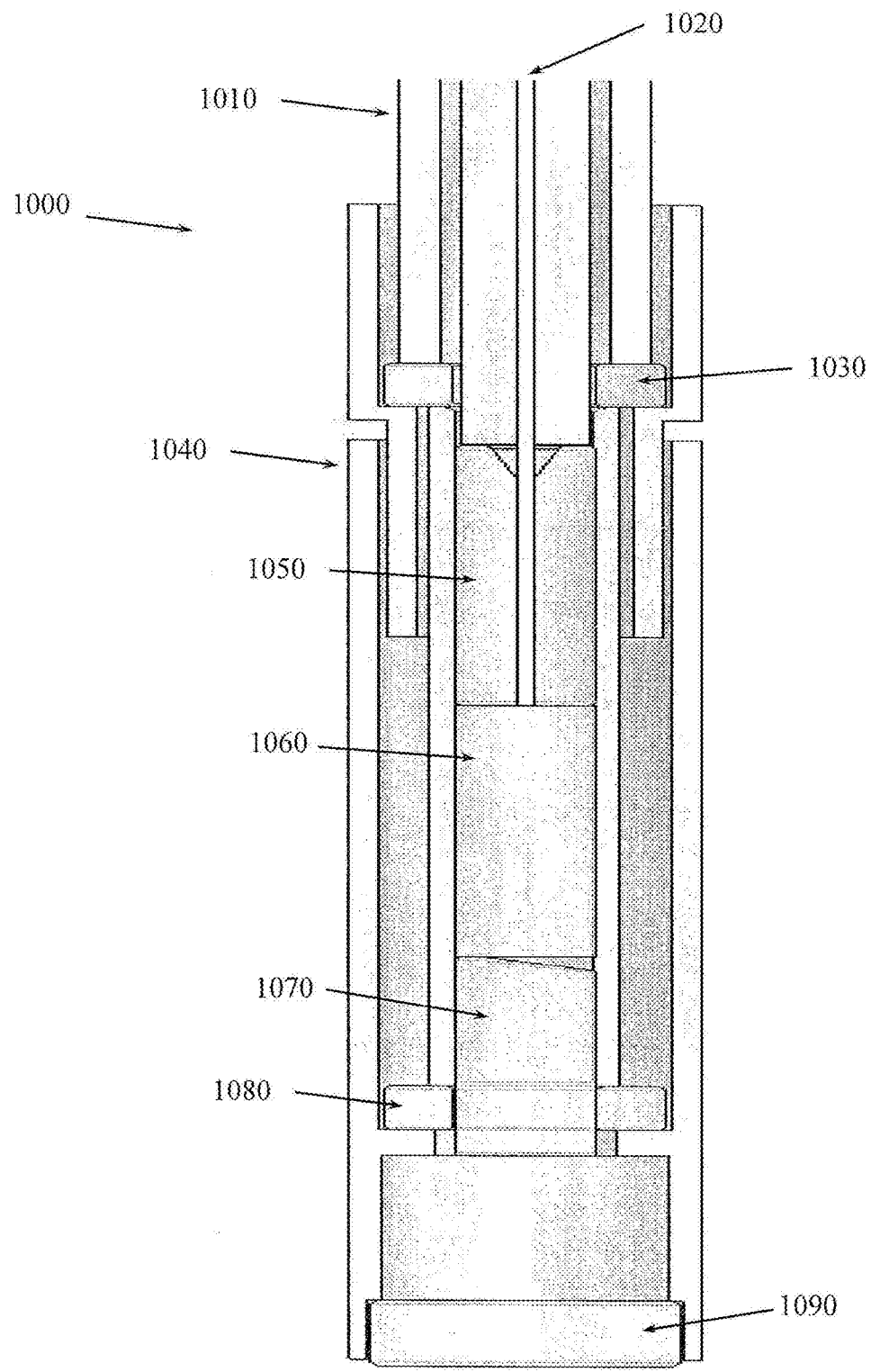
FIG. 10 illustrates another example of a catheter for acquiring OCT signals.

FIG. 10 illustrates another example catheter 1000 for acquiring OCT signals. The catheter 1000 includes sheath 1010. The composition of sheath 1010 may include, for example, polytetrafluoroethylene (PTFE), ceramic, polyetheretherketone (PEEK), an RF compatible material, and so on. An RF compatible material is a material that resists heating when RF energy is applied to the material. The catheter 1000 also includes a fiber optic cable 1020. The fiber optic cable 1020 may be, for example, SMF-28e cable with a tight buffer PVC, and so on. Ring jewel bearings 1030 and 1080 may be, for example, sapphire. The end cap 1040 protects the optical assembly from contamination. The catheter 1000 may include a ferrule 1050 that maintains the fiber optic cable 1020 in proper alignment. The optical assembly of the catheter 1000 may include a Gradient Index Lens (GRIN) 1060, a Risley prism 1070, and optical glass 1090.

Figure 11:
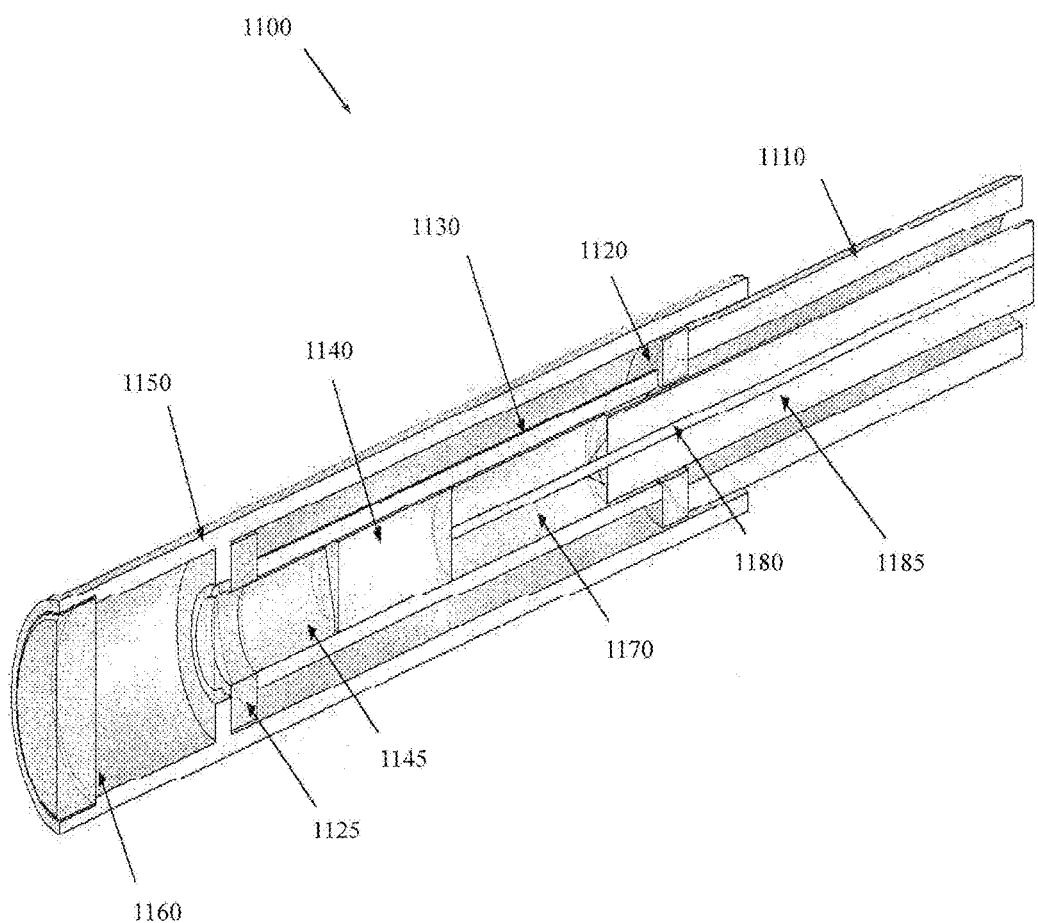
FIG. 11 illustrates an example catheter for acquiring OCT signals.

FIG. 11 illustrates an example catheter 1100 for acquiring OCT signals. The catheter 1100 may include, for example, a sheath 1110, a ring jewel bearing 1120, a ring jewel bearing 1125, a split sleeve 1130, a GRIN lens 1140, a Risley prism 1145, a sheath tip 1150, a window 1160, a ferrule 1170, and a fiber optic cable 1180 with a tight buffer 1185. The sheath 1110 may be composed of, for example, PTFE. The ring jewel bearings 1120 and 1125 may be composed of, for example, sapphire. The split sleeve 1130 may be, for example, ceramic. The sheath tip 1150 may be, for example, PEEK. The window 1160 may be, for example, fused silica. The ferrule 1170 may be, for example, glass or ceramic. The fiber optic cable 1180 may be, for example, a SMF-28e cable. The tight buffer 1185 may be, for example, PVC.

Catheter 1100 facilitates imaging a ROI with OCT using forward looking imaging. Forward looking imaging is imaging that occurs through the end of a catheter. To accomplish this, the fiber optic cable 1180 rotates within the sheath tip 1150 to perform a generally circular scan of the ROI. The ring jewel bearings 1120 and 1125 facilitate rotating when torque is applied to the fiber optic cable 1180. The ring jewel bearings 1120 and 1125 provide a low friction joint for rotating. Thus, the sheath tip 1150 remains stationary relative to the fiber optic cable 1180, GRIN lens 1140, Risley prism 1145, and ferrule 1170 when rotating the fiber optic cable 1180.

In one example, catheter 1100 has a rigid end length of 18 mm and an outer diameter of 2.5 mm. Catheter 1100 has a scan diameter of 2 mm, which results in a 6.28 mm lateral scanning range. Catheter 1100 maintains a FWHM spot size of less than 30 μm over an entire 1 mm working range. Images using forward looking imaging are acquired at 40 kHz line scan rate, 2000 lines per image, and 512 pixels per line. This corresponds to a 6 μm and 3.1 μm pixel size in the axial and lateral dimensions respectively. A correlation based method may be used to correct for non-uniform scanning rates, removing highly correlated axial scans.

Figure 12:
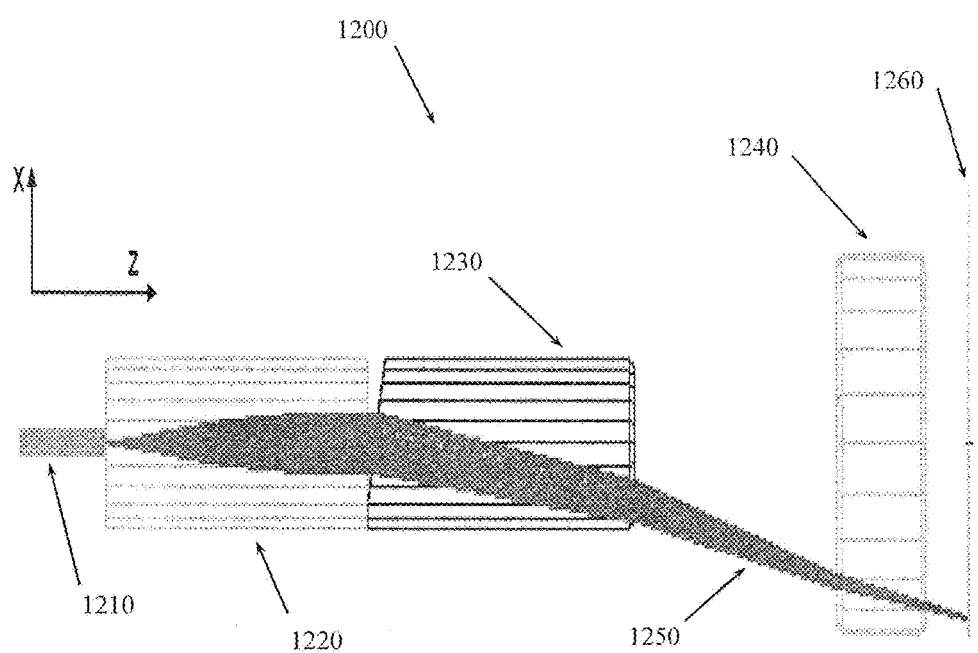
FIG. 12 illustrates an example optical assembly in a catheter for acquiring OCT signals.

FIG. 12 illustrates an optical assembly 1200 that can be used in a catheter for acquiring OCT signals. The optical assembly 1200 may include a fiber optic cable 1210, a GRIN lens 1220, a Risley prism 1230, and an optical glass window 1240. The optical assembly 1200 facilitates imaging a ROI 1260 with an optical signal 1250. Optical assembly 1200 may be used to perform generally circular scanning of ROI 1260. The rotating fiber optic cable 1210 also rotates GRIN lens 1220, Risley prism 1230, and to obtain the OCT signal 1250. Thus, the rotating fiber optic cable 1210 allows the optical assembly 1200 to facilitate imaging ROI 1260 in a generally circular pattern.

In one example, a flexible forward scanning OCT catheter may be designed for in-contact, circular-scan imaging in ex vivo or in vivo experiments. Ex vivo experiments may be conducted for varying time periods. In one example, ex vivo imaging is conducted for 90 seconds: 15 seconds prior to the start of RF energy delivery; 60 seconds during energy delivery; and 15 seconds after the conclusion of RF energy delivery. Ablation of material (e.g. myocardial tissue) with the purpose of forming a lesion is effective where the catheter is perpendicular to the material and there is adequate contact between the catheter and the material. In one example, ex vivo ablation lesions may be created with a temperature controlled protocol (e.g. 80° C.) with a maximum delivered power of 50 W.

Figure 14:
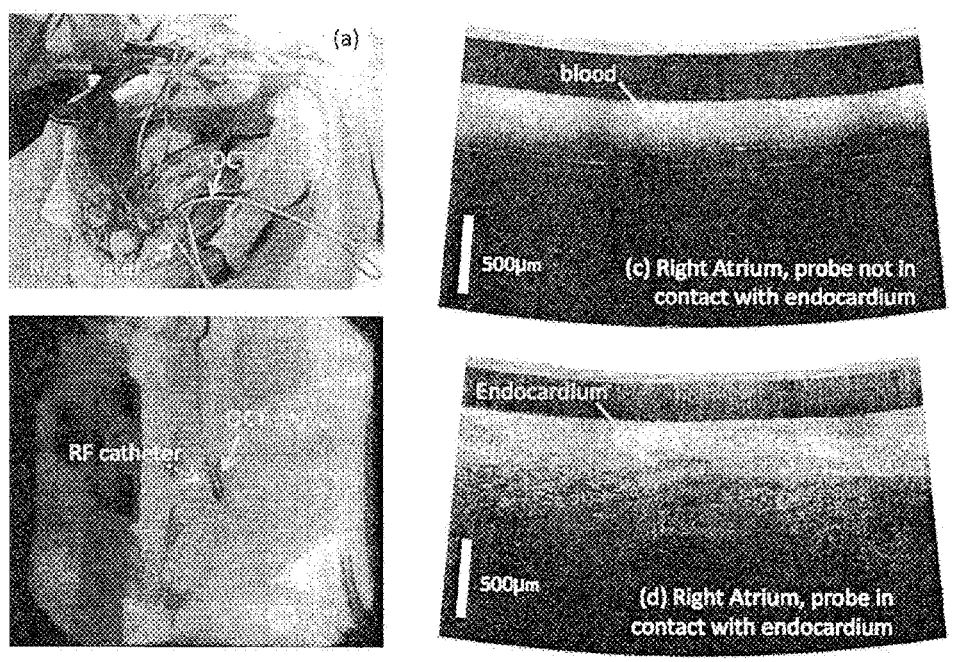
FIG. 14 illustrates an example in vivo experiment for acquiring OCT signals.

In vivo experiments, as show in FIG. 14, may also be conducted. In one example, to evaluate whether OCT can identify dynamic tissue change due to RF energy delivery in vivo, an RF ablation catheter may be inserted directly into a right porcine atrium, as shown in FIG. 14(a). The RF ablation catheter may be advanced and navigated within the heart under fluoroscopic guidance, as shown in FIG. 14(b). In one example, images of the endocardial surface and sub endocardial tissue may be obtained when the RF ablation catheter is in direct contact with the endocardial surface, as shown in FIG. 14(c). Image penetration may be significantly reduced due to blood absorption and scattering without direct contact, as shown in FIG. 14(d).

Figure 15:
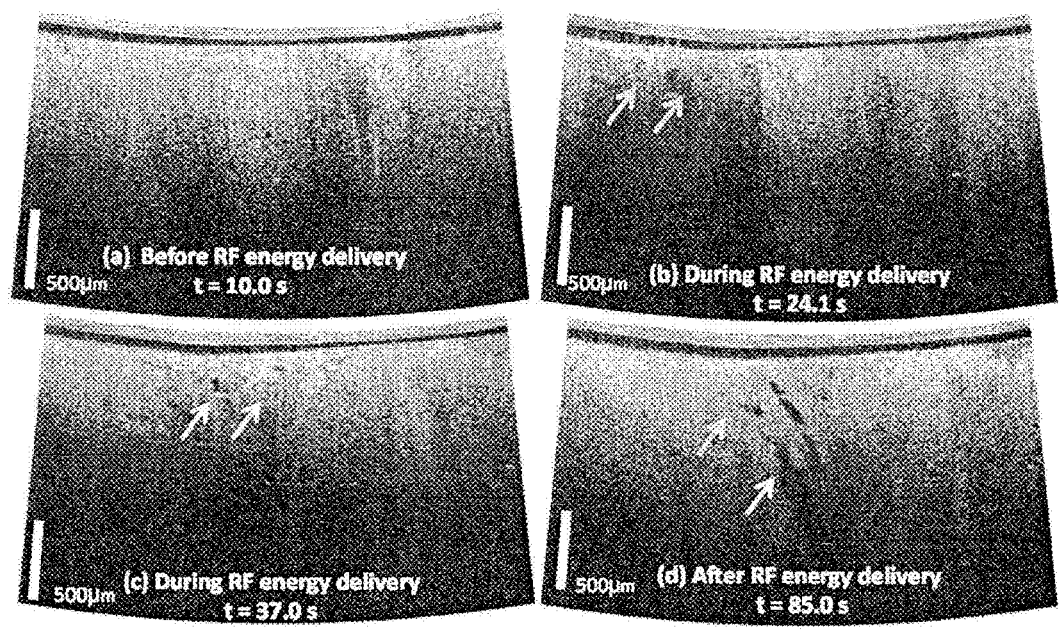
FIG. 15 illustrates an example in vivo experiment for acquiring OCT signals.

In one example, an in vivo experiment may be conducted with temperature controlled RF energy being delivered for 60 seconds, with a target temperature of 85° C., after 15 seconds of imaging with stable contact with the endocardial surface. The formation and progressive increase in size of cavities within tissue may be observed in OCT images like those of FIG. 14(c) and FIG. 14(d). Alternatively, the effects of the RF energy can be visualized at different time intervals as shown in FIG. 15.

Figure 13:
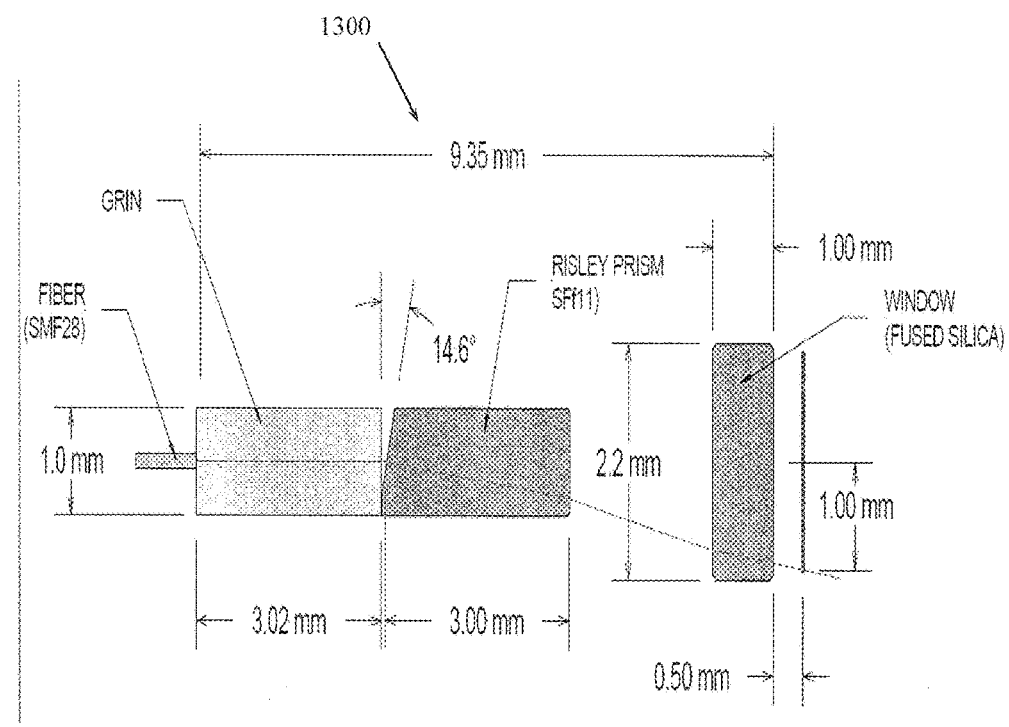
FIG. 13 illustrates one specific example of an optical assembly in a catheter for acquiring OCT signals.

FIG. 13 illustrates one specific embodiment of an optical assembly 1300 in a catheter for acquiring OCT signals. Optical assembly 1300 may include, for example, a fiber optic cable, a GRIN lens, a Risley prism, and an optical window composed of, for example, fused silica.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and apparatus described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A system comprising:
an ablation catheter comprising:
an ablation mechanism to ablate a region of interest (ROI) in a material; and
an optical coherence tomography (OCT) device to acquire an OCT signal from the ablated ROI; and
a computer apparatus coupled to the OCT device to determine a development stage of a lesion formed in the ablated ROI by analyzing an optical property of the ROI as recorded in the OCT signal.

2. The system of claim 1, wherein the development stage is determined by the apparatus based on at least one of a size of the lesion and a length of the lesion.

3. The system of claim 1, wherein the ablation mechanism employs at least one of Radio Frequency Ablation (RFA), High Intensity Focused Ultrasound (HIFU) ablation, laser ablation, and cryoablation.

4. The system of claim 1, wherein the material is myocardial tissue.

5. The system of claim 1, wherein the OCT device comprises an OCT detector.

6. The system of claim 1, wherein the optical property comprises at least one of birefringence, anisotropy, absorption, light attenuation rate, backscattering, tissue scattering, mean intensity, and tissue heterogeneity.

7. The system of claim 1, wherein the OCT device comprises an optical assembly coupled to an optical fiber and the ablation mechanism comprises a radio frequency ablation device that delivers radio frequency energy suitable to ablate the ROI.

8. The system of claim 7, wherein the optical fiber and the radio frequency ablation device are enclosed within the ablation catheter.

9. The system of claim 8, wherein the ablation catheter comprises a magnetic resonance imaging and radio frequency energy compatible catheter device.

10. The system of claim 7, wherein the optical assembly is configured to rotate the optical fiber to provide a circular, forward-looking image of the ROI.

11. The system of claim 7, wherein the optical assembly comprises a sheath tip, a GRIN lens, a Risley prism, and a ferrule, and
wherein the sheath tip is stationary with respect to the fiber optic cable.

12. A method comprising:
controlling a detector within an ablation catheter to acquire an optical coherence tomography OCT signal from a region of interest (ROI) in a material that has been or is being ablated by an ablation mechanism within the ablation catheter, wherein the ablation catheter is in direct contact with the material; and
controlling an apparatus coupled to the detector to determine a development stage of a lesion in the ROI due to the ablating as a function of analyzing an optical property of the lesion based on the OCT signal.

13. The method of claim 12, wherein the detector performs a circular-scan imaging procedure.

14. The method of claim 12, further comprising controlling the apparatus to stop the ablating upon determining that the lesion is a clinically relevant lesion or a borderline overtreatment lesion based on the optical property.

15. The method of claim 12, wherein the optical property comprises at least one of birefringence, anisotropy, absorption, light attenuation rate, backscattering, tissue scattering, mean intensity, and tissue heterogeneity.

16. The method of claim 12, wherein the material comprises myocardial tissue.

* * * * *

(12) EX PARTE REEXAMINATION CERTIFICATE (208th)
Ex Parte Reexamination Ordered under 35 U.S.C. 257

United States Patent
Rollins et al.

(10) Number: US 9,883,901 C1
(45) Certificate Issued: *Mar. 8, 2022

(54) CHARACTERIZING ABLATION LESIONS USING OPTICAL COHERENCE TOMOGRAPHY (OCT)

(71) Applicant: CASE WESTERN RESERVE UNIVERSITY, Cleveland, OH (US)

(72) Inventors: Andrew M. Rollins, Cleveland Heights, OH (US); Christine P. Fleming, Bronx, NY (US)

(73) Assignee: CASE WESTERN RESERVE UNIVERSITY, Cleveland, OH (US)

Supplemental Examination Request:
No. 96/000,354, Mar. 12, 2021

Reexamination Certificate for:
Patent No.: 9,883,901
Issued: Feb. 6, 2018
Appl. No.: 14/674,539
Filed: Mar. 31, 2015

(*) Notice: This patent is subject to a terminal disclaimer.

Related U.S. Application Data

(63) Continuation of application No. 12/844,944, filed on Jul. 28, 2010, now Pat. No. 9,089,331.

(60) Provisional application No. 61/230,281, filed on Jul. 31, 2009.

(51) Int. Cl.
*A61B 18/18* (2006.01)
*A61B 18/12* (2006.01)
*A61B 5/00* (2006.01)
*A61B 18/14* (2006.01)
*A61B 17/00* (2006.01)
*A61B 18/00* (2006.01)
*A61B 18/02* (2006.01)
*A61B 18/20* (2006.01)
*A61B 90/00* (2016.01)

(52) U.S. Cl.
CPC ............ *A61B 18/12* (2013.01); *A61B 5/0066* (2013.01); *A61B 5/6852* (2013.01); *A61B 18/1492* (2013.01); *A61B 18/02* (2013.01); *A61B 18/20* (2013.01); *A61B 2017/00243* (2013.01); *A61B 2018/00351* (2013.01); *A61B 2018/00702* (2013.01); *A61B 2090/3735* (2016.02)

(58) Field of Classification Search
None
See application file for complete search history.

(56) References Cited

To view the complete listing of prior art documents cited during the supplemental examination proceeding and the resulting reexamination proceeding for Control Number 96/000,354, please refer to the USPTO's public Patent Application Information Retrieval (PAIR) system under the Display References tab.

*Primary Examiner* — Robert L Nasser

(57) ABSTRACT

Systems, methods, and other embodiments associated with characterizing Radio Frequency Ablation (RFA) lesions using Optical Coherence Tomography (OCT) are described. One example method includes acquiring an OCT signal from a Region Of Interest (ROI) in an ablated material. The example method may also include determining whether a lesion was formed by the ablation by analyzing optical properties of the ROI as recorded in the OCT signal.

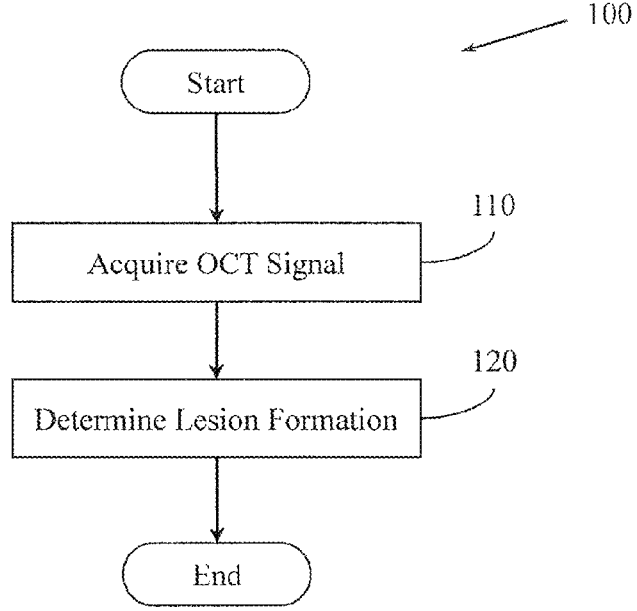

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

Claims 2-7 and 12-16 are determined to be patentable as amended.

Claims 8-11, dependent on an amended claim, are determined to be patentable.

New claims 17-24 are added and determined to be patentable.

2. [The system of claim 1] *A system comprising:*
an ablation catheter comprising:
   an ablation mechanism to ablate a region of interest (ROI) in a material; and
   an optical coherence tomography (OCT) device to acquire an OCT signal from the ablated ROI; and
a computer apparatus coupled to the OCT device to determine a development stage of a lesion formed in the ablated ROI by analyzing optical properties of the ROI as recorded in the OCT signal,
wherein the development stage is determined by the apparatus based on at least one of a size of the lesion and a [length] *depth* of the lesion, *and wherein the optical properties comprise anisotropy and tissue heterogeneity*.

3. [The system of claim 1] *A system comprising:*
an ablation catheter comprising:
   an ablation mechanism to ablate a region of interest (ROI) in a material; and
   an optical coherence tomography (OCT) device to acquire an OCT signal from the ablated ROI; and
a computer apparatus coupled to the OCT device to determine a development stage of a lesion formed in the ablated ROI by analyzing optical properties of the ROI as recorded in the OCT signal,
wherein the ablation mechanism employs at least one of Radio Frequency Ablation (RFA), High Intensity Focused Ultrasound (HIFU) ablation, laser ablation, and cryoablation, *and wherein the optical properties comprise birefringence, anisotropy, and tissue heterogeneity*.

4. The system of claim [1] *2*, wherein the material is myocardial tissue, *and wherein determining the development stage of the lesion formed in the ablated ROI by analyzing the optical properties of the ROI as recorded in the OCT signal comprise identifying viable myocardial tissue based on a polarization artifact and identifying myocardial tissue with the lesion based on the polarization artifact being lost*.

5. The system of claim [1] *2*, wherein the OCT device comprises an OCT detector, *and wherein the optical properties comprise birefringence*.

6. The system of claim [1] *2*, wherein the optical [property comprises] *properties further comprise* at least one of birefringence, [anisotropy,] absorption, light attenuation rate, backscattering, tissue scattering, *and* mean intensity[, and tissue heterogeneity].

7. The system of claim [1] *2*, wherein the OCT device comprises an optical assembly coupled to an optical fiber and the ablation mechanism comprises a radio frequency ablation device that delivers radio frequency energy suitable to ablate the ROI.

12. A method comprising:
   controlling a detector within an ablation catheter to acquire an optical coherence tomography OCT signal from a region of interest (ROI) in a material that has been or is being ablated by an ablation mechanism within the ablation catheter, wherein the ablation catheter is in direct contact with the material; and
   controlling an apparatus coupled to the detector to determine a development stage of a lesion in the ROI due to the ablating as a function of analyzing [an optical property] *optical properties* of the lesion based on the OCT signal, *the optical properties comprising anisotropy and tissue heterogeneity*.

13. [The method of claim 12] *A method comprising:*
   controlling a detector within an ablation catheter to acquire an optical coherence tomography OCT signal from a region of interest (ROI) in a material that has been or is being ablated by an ablation mechanism within the ablation catheter, wherein the ablation catheter is in direct contact with the material; and
   controlling an apparatus coupled to the detector to determine a development stage of a lesion in the ROI due to the ablating as a function of analyzing optical properties of the lesion based on the OCT signal,
   wherein the detector performs a circular-scan imaging procedure, *and wherein the optical properties comprise birefringence and/or anisotropy, and further comprises gradient strength*.

14. [The method of claim 12, further comprising] *A method comprising:*
   controlling a detector within an ablation catheter to acquire an optical coherence tomography OCT signal from a region of interest (ROI) in a material that has been or is being ablated by an ablation mechanism within the ablation catheter, wherein the ablation catheter is in direct contact with the material; and
   controlling an apparatus coupled to the detector to determine a development stage of a lesion in the ROI due to the ablating as a function of analyzing an optical property of the lesion based on the OCT signal; and
   controlling the apparatus to stop the ablating upon determining that the lesion is a clinically relevant lesion or a borderline overtreatment lesion based on the optical property, *and wherein the optical property further comprises light attenuation rate*.

15. The method of claim 12, wherein the optical [property comprises] *properties further comprise* at least one of [birefringence, anisotropy,] absorption, light attenuation rate, backscattering, tissue scattering, mean intensity, and [tissue heterogeneity] *birefringence*.

16. The method of claim 12, wherein the material comprises myocardial tissue, *and further comprising identifying viable myocardial tissue based on identifying a polarization artifact as recorded in the OCT signal and identifying myocardial tissue with the lesion based on the polarization artifact being lost*.

17. A system comprising:
    an ablation catheter comprising:
        an ablation mechanism to ablate a region of interest (ROI) in a material; and
        an optical coherence tomography (OCT) device to acquire an OCT signal from the ablated ROI; and
    a computer apparatus coupled to the OCT device to determine a development stage of a lesion formed in the ablated ROI by analyzing anisotropy of the ROI as recorded in the OCT signal and determining tissue architecture, wherein the OCT device comprises an optical assembly coupled to an optical fiber and the ablation mechanism comprises a radio frequency ablation device that delivers radio frequency energy suitable to ablate the ROI, and wherein the optical assembly is configured to rotate the optical fiber to provide a circular, forward-looking image of the ROI.

18. The system of claim 17, wherein the ablation mechanism employs at least one of Radio Frequency Ablation (RFA), High Intensity Focused Ultrasound (HIFU) ablation, laser ablation, and cryoablation.

19. The system of claim 17, wherein the material is myocardial tissue.

20. The system of claim 17, wherein the OCT device comprises an OCT detector.

21. The system of claim 17, wherein the OCT device comprises an optical assembly coupled to an optical fiber and the ablation mechanism comprises a radio frequency ablation device that delivers radio frequency energy suitable to ablate the ROI.

22. The system of claim 21, wherein the optical fiber and the radio frequency ablation device are enclosed within the ablation catheter.

23. The system of claim 22, wherein the ablation catheter comprises a magnetic resonance imaging and radio frequency energy compatible catheter device.

24. A system comprising:
    an ablation catheter comprising:
        an ablation mechanism to ablate a region of interest (ROI) in a material; and
        an optical coherence tomography (OCT) device to acquire an OCT signal from the ablated ROI; and
    a computer apparatus coupled to the OCT device to determine a development stage of a lesion formed in the ablated ROI by analyzing anisotropy of the ROI as recorded in the OCT signal and determining tissue architecture,
    wherein the development stage is determined by the apparatus based on at least one of a size of the lesion and a depth of the lesion,
    wherein the OCT device comprises an optical assembly coupled to an optical fiber and the ablation mechanism comprises a radio frequency ablation device that delivers radio frequency energy suitable to ablate the ROI,
    wherein the optical assembly comprises a sheath tip, a GRIN lens, a Risley prism, and a ferrule, and
    wherein the sheath tip is stationary with respect to the fiber optic cable.

* * * * *